US008813550B2

(12) United States Patent
Lindsay

(10) Patent No.: US 8,813,550 B2
(45) Date of Patent: Aug. 26, 2014

(54) SHEAROGRAPHIC IMAGING MACHINE AND METHOD

(71) Applicant: Bridgestone Bandag, LLC, Muscatine, IA (US)

(72) Inventor: John S. Lindsay, Muscatine, IA (US)

(73) Assignee: Bridgestone Bandag, LLC, Muscatine, IA (US)

( * ) Notice: Subject to any disclaimer, the term of this patent is extended or adjusted under 35 U.S.C. 154(b) by 0 days.

(21) Appl. No.: 13/906,823

(22) Filed: May 31, 2013

(65) Prior Publication Data
US 2013/0319101 A1 Dec. 5, 2013

Related U.S. Application Data

(60) Provisional application No. 61/654,475, filed on Jun. 1, 2012.

(51) Int. Cl.
*G01M 17/02* (2006.01)
*B60C 23/02* (2006.01)
*G01B 9/02* (2006.01)

(52) U.S. Cl.
CPC .................... *G01M 17/027* (2013.01)
USPC .............. 73/146; 356/458; 356/457; 356/520

(58) Field of Classification Search
USPC .................................... 73/146–146.8
See application file for complete search history.

(56) References Cited

U.S. PATENT DOCUMENTS

| 4,702,594 | A | 10/1987 | Grant |
| 5,373,729 | A | 12/1994 | Seigeot |
| 6,330,822 | B1 | 12/2001 | Hawk et al. |
| 6,840,097 | B1 | 1/2005 | Huber et al. |
| 2001/0021025 | A1* | 9/2001 | Lindsay et al. ............... 356/458 |
| 2001/0040682 | A1* | 11/2001 | Lindsay et al. ............... 356/520 |
| 2005/0052637 | A1* | 3/2005 | Shaw et al. .................. 356/35.5 |
| 2005/0200838 | A1* | 9/2005 | Shaw et al. ................. 356/237.1 |
| 2005/0264796 | A1* | 12/2005 | Shaw et al. ................. 356/237.2 |
| 2008/0147347 | A1* | 6/2008 | Shaw et al. .................... 702/108 |
| 2008/0158569 | A1* | 7/2008 | Maehner et al. ............. 356/458 |
| 2008/0202229 | A1* | 8/2008 | Maehner et al. ............... 73/146 |

OTHER PUBLICATIONS

Ahn Jae Yul; International Search Report and Written Opinion; Aug. 27, 2013; pp. 1-9; Korean Intellectual Property Office; Daejeon Metropolitan City, Republic of Korea.

* cited by examiner

Primary Examiner — Andre Allen

(57) ABSTRACT

A tire inspection machine includes an incoming conveyor adapted to transport tires to the machine and also align the tires in a transverse direction. An inspection table of the machine includes a table conveyor system that is responsive to a controller. The table and table conveyor are together arranged to permit scanning of both sidewall portions of a tire disposed thereon. A sensor detects a longitudinal position of the tire and stops the table conveyor when the tire is longitudinally aligned. A controller operates the table conveyor based on the longitudinal position of the tire.

20 Claims, 4 Drawing Sheets

SHEAROGRAPHIC IMAGING MACHINE AND METHOD

CROSS-REFERENCE TO RELATED APPLICATIONS

This patent application claims the benefit of U.S. Provisional Patent Application No. 61/654,475, filed Jun. 1, 2012, which is incorporated herein in its entirety by this reference.

TECHNICAL FIELD

This patent disclosure relates generally to an apparatus for inspecting articles and, more particularly, to a shearographic machine for inspecting tires or tire casings as part of a tire retread process.

BACKGROUND

The technique of shearing interferometry, a process which is commonly referred to as shearography, typically involves the interference of two laterally displaced images of the same object to form an interference image. Conventional shearographic methods include taking a first interference image (or baseline image) be taken while the object is in an unstressed or first stressed condition and another interference image while the object is in a second stressed condition. Comparison of these two interference images, for example, by methods of image subtraction, reveals information about the presence of certain defects in the composite tire or casing material in a single image called a shearogram. In particular, shearography has been shown to be useful to detect defects in vehicle tires, especially retread vehicle tires.

In conventional electronic shearography machines, a tire or tire casing is loaded onto an inspection table. The table may include a radiation emitter and receiver assembly that can be raised relative to the table within a central opening of the casing and can be rotated relative to the tire to permit inspection of the entire surface of the tire. Typically, shearography machines include a chamber that can enclose the tire such that a vacuum may be applied to the tire. Most tire defects, such as material layer separation, will result in air being trapped within the tire material. This trapped air will cause bulges to appear when the tire is subjected to a vacuum or dimples when the tire is subjected to positive gage pressure within the enclosure. These bulges or dimples can then be detected by the shearographic process. One example of a known shearographic machine can be found in U.S. Pat. No. 6,791,695 (the '695 patent), which is incorporated herein in its entirety by reference.

In typical shearographic inspection machines, such as the machines described in the '695 patent, a clamshell enclosure is used to house the tire during the inspection process. With the clamshell open, loading and unloading a tire into and out of the machine involves placing the tire onto a moveable tray that tilts into and out from the clamshell enclosure. The moveable tray includes pins that center or otherwise position the tire within the enclosure to provide an appropriate distance between the various surfaces of the tire and the shearographic emitter/receiver. When the tray is tilted out of the enclosure, an operator may manually load and unload the tire from the tray.

In the known inspection machines, the handling time for each tire from loading into the machine to unloading out of the machine can take between forty seconds to several minutes. During this time, the inspection machine is not operating to inspect tires, which can result in relatively high "dead" times and relatively low inspection rate throughputs for the machines.

SUMMARY

In one aspect, the disclosure describes a tire or casing inspection machine. The inspection machine includes a sealable enclosure formed within a housing. The sealable enclosure is adapted to be selectively subjected to positive gage pressure and/or vacuum when shearographically testing a tire or casing disposed within the sealable enclosure. A table disposed within the sealable enclosure is connected to a portion of the housing and has an opening that is adapted to be aligned with a bead hole of the tire or casing disposed on the table. A shearographic assembly is connected to the housing and disposed within the sealable enclosure in alignment with the opening of the table. The shearographic assembly is selectively moveable to protrude through the opening relative to the table and rotatable about an opening centerline such that it can scan multiple portions of the tire or casing disposed on the table from various perspectives. At least two conveyor strips extend parallel to one another and are associated with the table. The at least two conveyor strips are sized and positioned on the table such that they do not interfere with visibility of top and bottom sidewall portions of the tire or casing disposed on the table relative to the shearographic assembly. The at least two conveyor strips are adapted to carry and selectively move the tire or casing relative to the machine.

In another aspect, the disclosure describes a method for inspecting tires or casings. The method includes staging a tire adjacent an inspection machine, which has a sealable enclosure. The tire is automatically advanced towards the inspection machine when an inspection cycle is initiated. The tire is aligned in a transverse direction relative to the inspection machine while being advanced towards the inspection machine. The sealable enclosure is opened to admit the tire onto an inspection table having a table opening. The tire is admitted onto the inspection table in a transversely aligned condition relative to the table opening, and the sealable enclosure is closed. The tire is conveyed on the table in a longitudinal direction. The longitudinal position of the tire relative to the table opening is sensed. The tire is sufficiently conveyed along the table until the tire is longitudinally aligned tire with the table opening. An inspection device is activated to inspect the tire while the tire is longitudinally and transversely aligned with the table opening.

In yet another aspect, the disclosure describes a shearographic inspection machine. The machine includes an enclosure formed within a housing. The enclosure is adapted to be selectively subjected to pressure or vacuum when testing a tire or casing disposed within the enclosure. The enclosure has a domed top portion and a generally cylindrical bottom portion, which are sealably engageable along respective rims. A generally circular table is disposed within the enclosure and has a central opening that is adapted to be aligned with a bead hole of the tire or casing disposed on the table. In one embodiment, the table is coplanar with the rim of the generally cylindrical bottom portion of the enclosure.

A shearographic assembly is connected to the housing and disposed within the enclosure. The shearographic assembly is aligned with a centerline of the central opening, moveable to protrude through the opening relative to the table, and rotatable about the centerline such that it can scan multiple portions of the tire or casing disposed on the table from various perspectives. Four conveyor strips extend parallel to one another and are associated with the table. The four conveyor strips are sized and positioned on the table such that they do not interfere with visibility of top and bottom sidewall portions of the tire or casing disposed on the table relative to the shearographic assembly. The four conveyor strips are adapted to carry and selectively move the tire or casing relative to the machine.

An incoming conveyor is disposed adjacent the housing and adapted to stage and deliver the tire or casing to the at least two conveyor strips. A centering device is disposed along the incoming conveyor and configured to align the tire or casing in a transverse direction, where the transverse direction is perpendicular to a longitudinal direction of travel defined by the four conveyor strips. A controller is associated with the shearographic assembly and the four conveyor strips, and a sensor is disposed to sense a position of the tire or casing relative to the table and provide a signal indicative of the position to the controller. The controller is disposed to position the tire or casing such that the bead hole is substantially aligned with the central opening in the table by activating the at least two conveyor strips to carry the tire or casing, and to activate the shearographic assembly to protrude from the table and be disposed within the bead hole for scanning the tire or casing.

In one embodiment, the disclosure describes a tire or casing inspection machine that includes a shearographic assembly adapted to move along an axis within a machine enclosure. The machine enclosure is configured to expose a tire disposed therein in surrounding relation relative to the shearographic assembly to one or more different pressure conditions. The inspection machine includes an incoming conveyor, an alignment device, an inspection table disposed within the machine enclosure, a table conveyor system associated with the table, a sensor, and a controller.

The incoming conveyor is adapted to transport a tire or casing along a longitudinal direction toward the machine enclosure. The alignment device is associated with the incoming conveyor and is adapted to align the tire or casing with the shearographic assembly in a transverse direction while the tire or casing is carried by the incoming conveyor toward the machine enclosure. The inspection table has an opening that is substantially aligned with the shearographic assembly and is adapted to allow the shearographic assembly to scan a bottom sidewall portion of the tire. The inspection table further includes a tire-facing surface. The table conveyor system includes at least two conveyor belts extending in parallel to one another across the tire-facing surface and around two sides of the opening such that the at least two conveyor belts do not interfere with a scanning operation of both sidewall portions of the tire by the shearographic assembly. The conveyors are responsive to command signals. The sensor is associated with the machine and adapted to sense and provide position signals indicative of a longitudinal position of the tire or casing relative to the shearographic assembly. The controller is disposed to provide the command signals based on the position signals such that the table conveyor system operates to place the tire in a substantially longitudinally aligned position relative to the shearographic assembly.

In another embodiment, the disclosure describes a method for operating a tire or casing inspection machine. The method includes various process steps that can be carried out in any suitable order. In one embodiment, the steps include placing the tire or casing on an incoming conveyor, and advancing the tire or casing toward a machine enclosure of the inspection machine with the incoming conveyor. The tire or casing is displaced in a transverse direction so as to become transversely aligned with an inspection assembly of the machine enclosure. The transverse displacement may be carried out while the tire or casing is being advanced on the incoming conveyor. The tire or casing passes from the incoming conveyor to a table conveyor, which is associated with a table disposed within the machine enclosure and around the inspection assembly. The table includes a central opening around which the table conveyor is arranged such that both sidewall portions of the tire or casing are visible to a scanner of the machine while the tire is disposed on the table conveyor. A longitudinal position of the tire or casing relative to the table conveyor is sensed, and position signals indicative of the longitudinal position are provided to a controller. The controller is adapted to adjust operation of the table conveyor based on the position signals such that the tire or casing is placed in substantial longitudinal alignment with the inspection assembly.

DETAILED DESCRIPTION

Figure 1:
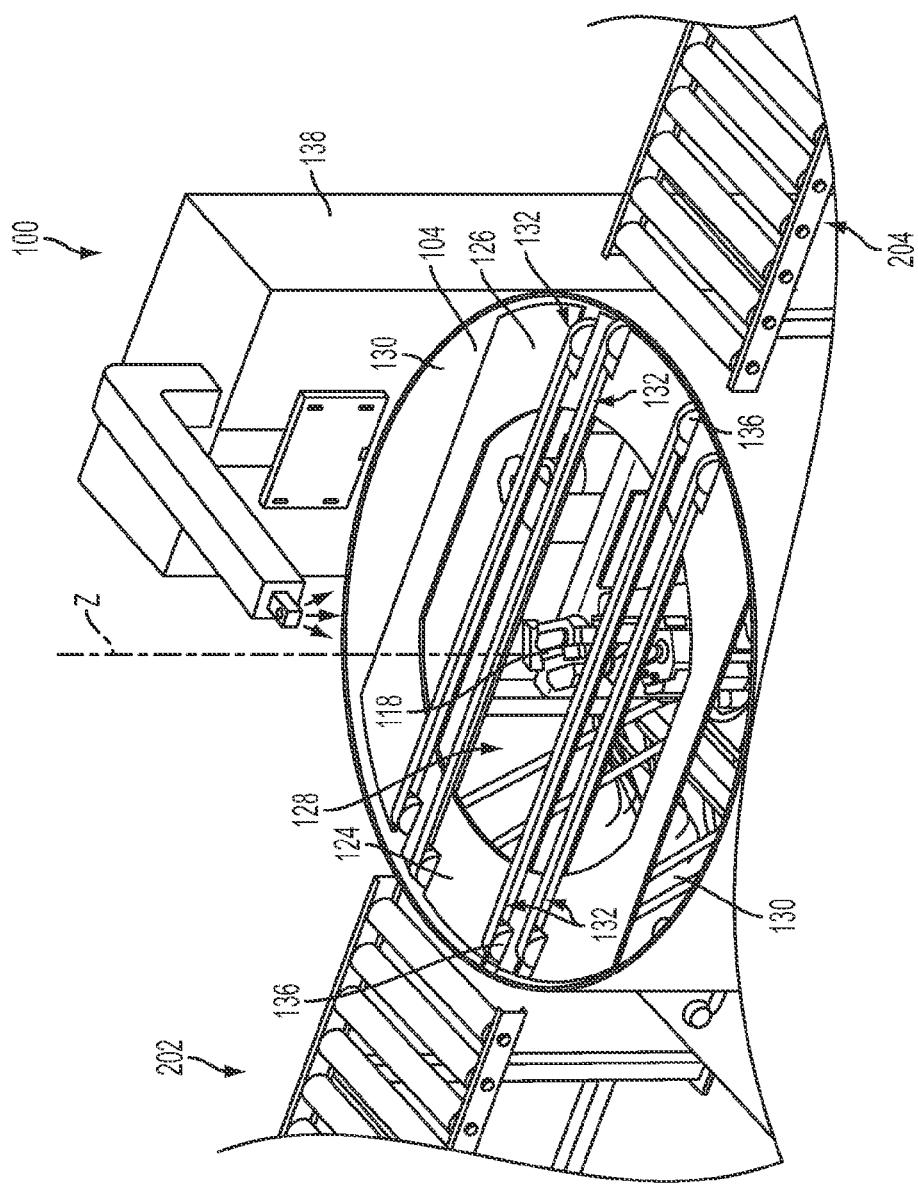
FIGS. 1, 2 and 3 are outline views from different perspectives of an embodiment of a shearographic tire imaging machine in accordance with principles of the disclosure.
Figure 2:
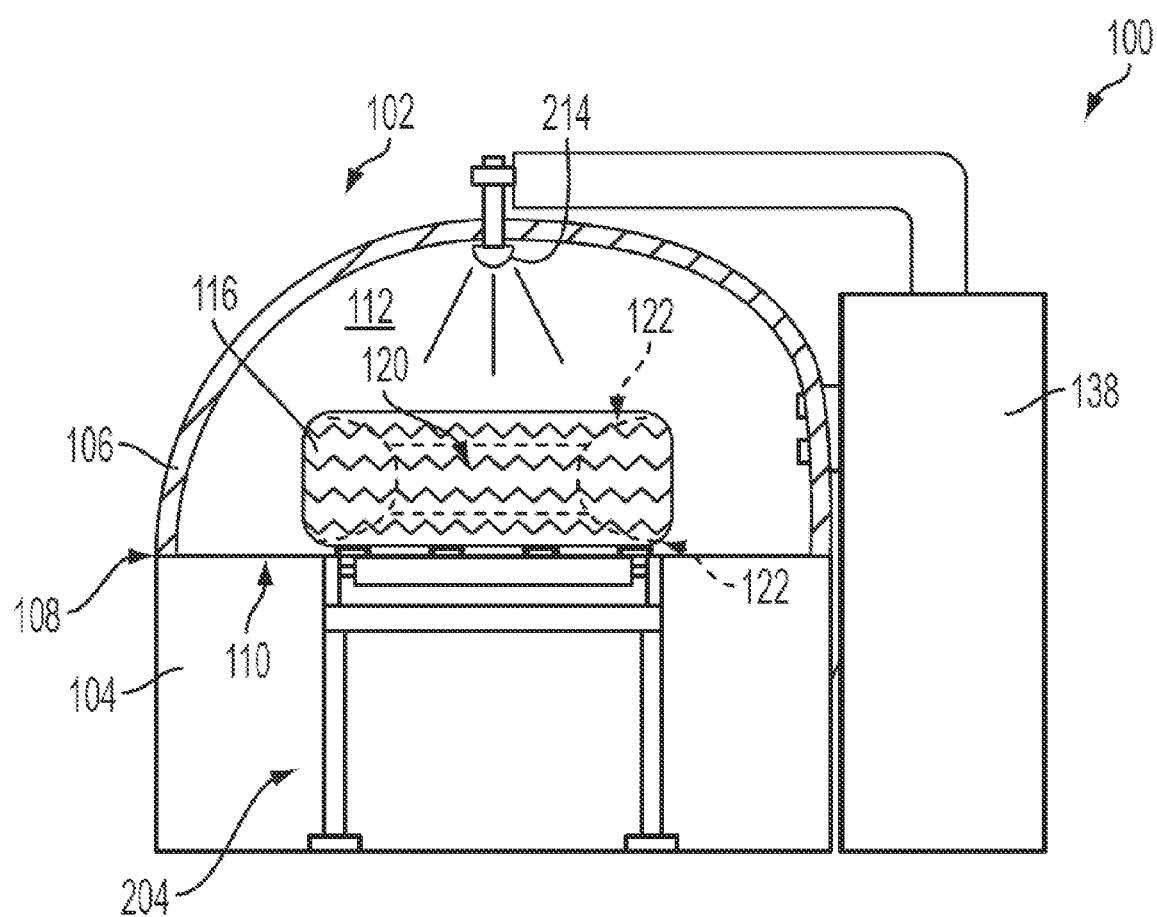
Figure 3:
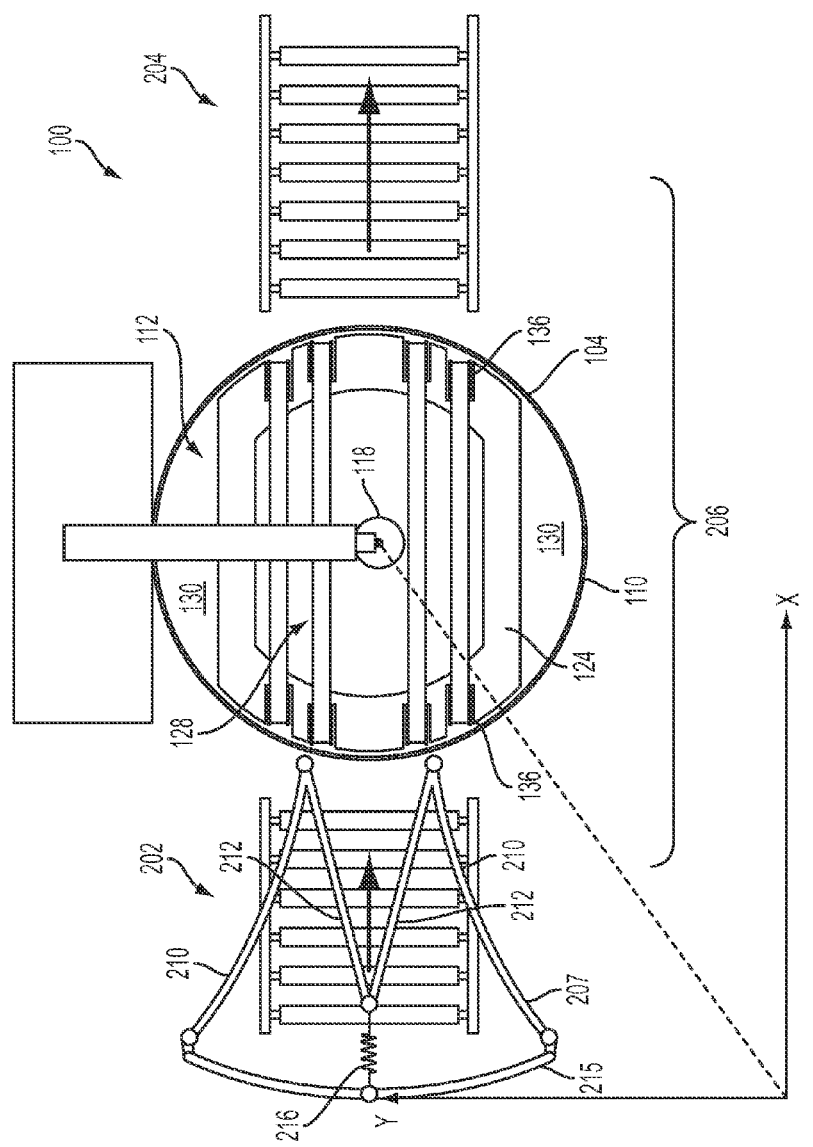

This disclosure relates to inspection machines and methods and, more particularly, to shearographic tire inspection machines and methods for staging tires for automatic loading and unloading from an inspection machine in an expeditious fashion that can reduce machine dead time and increase throughput. Outline views of a machine 100 are shown in FIGS. 1, 2 and 3 from various perspectives and with certain components removed for clarity. The machine 100 is a shearographic tire inspection machine that includes an enclosure 102 defined between lower and upper shells 104 and 106, respectively. The illustrated upper shell 106 is includes a generally convex exterior surface and a generally concave interior surface and is hingeably connected to the lower shell 104. The upper shell 106 has a rim 108 that sealably engages a corresponding rim 110 of the lower shell 104 such that, when the lower and upper shells 104 and 106 are mated, a clamshell-type enclosure 112 is formed, the interior of which can be selectively subjected to positive gage pressure and/or vacuum when testing a tire 116.

In other embodiments, the enclosure 112 can have different forms. For example, in some embodiments, the enclosure 112 can comprise a housing having moveable doors that are movable over a range of travel between an open position and a closed position to allow loading, unloading and testing of tires within the machine. In other embodiments, the enclosure 112 can include a dome-like upper shell that is reciprocally movable over a range of travel between an engaged position, in which the upper shell sealably engages the lower shell, and a disengaged position, in which the upper shell is displaced from the lower shell to allow a tire to pass between the lower shell and the upper shell. In yet other embodiments, the enclosure 112 can have other configurations. In various embodiments, opening or closing of the enclosure 112 in any configuration can be carried out automatically or manually.

One portion of the interior of the enclosure 112 houses a shearographic assembly 118, which can include one or more emitters of radiation such as laser light, e.g., and one or more receivers such as cameras, e.g. The shearographic assembly 118 is configured to move relative to the machine 100, for example, vertically, and also rotate relative thereto such that it can effectively scan multiple portions of a tire placed in the machine from various perspectives. The illustrated shearographic assembly 118 is in a retracted position in FIG. 1 in a depressed state within the lower shell 104. When a tire 116 is placed in the machine 100, for example, as shown in FIG. 2, the shearographic assembly 118 can be selectively raised to protrude through the casing bead hole 120 of the tire 116 to enable scanning of various surfaces of the tire 116. In the illustrated embodiment, the shearographic assembly 118 can be operated at two different heights relative to the tire such that both sidewall portions 122 of the tire 116 can be scanned without moving or flipping the tire within the machine. In other embodiments, different orientations and/or sensing positions of the tire, shearographic assembly and/or machine can be used.

As shown in FIG. 1, the machine 100 includes a table 124 having a shape that is generally compatible with the cross section of the enclosure 112 such that it fits entirely within the enclosure 112 when the upper and lower shells 106 and 104 are in the closed position. In the illustrated embodiment, the enclosure 112 has a generally cylindrical shape at the region surrounding the table 124 and the table 124 has a generally circular shape that fits within an inner diameter of the enclosure 112. The rim 110 of the lower shell 104 is disposed in substantially coplanar relationship to a generally flat, tire-facing surface 126 of the table 124, and both are generally perpendicular relative to a displacement axis Z of the shearographic assembly 118. The tire-facing surface 126 forms a central opening 128 that is generally aligned with the direction in which the shearographic assembly 118 moves such that, when a tire is placed on the tire-facing surface 126 of the table 124, the casing bead hole 120 is generally aligned with the central opening 128 to permit the shearographic assembly 118 to pass through the central opening 128 and move through the tire 116. Advantageously, the size and shape of the central opening 128 is configured to make visible both the top and bottom sidewall portions of the tire, while the tire is position on the table, to the shearographic assembly 118 during an inspection process. In the illustrated embodiment, the table 124 further includes two edge openings 130, which are embodied as arcuate sections that have been removed along respective chords of the table 124 at two opposite edges thereof.

The table 124 includes four conveyor strips 132, which extend parallel to one another along a longitudinal direction, X, as illustrated in the top view of FIG. 3. The illustrated placement and configuration of the conveyor strips 132 is but one configuration that is possible. The conveyor strips can be sized and positioned on the table such that they do not interfere with visibility of the top and bottom sidewall portions of the tire relative to the shearographic assembly 118. In other words, the conveyor strips can permit the substantially unhindered view of both sidewall portions of a tire in position for inspecting by the shearographic assembly 118. In the embodiment shown in FIG. 3, each conveyor strip 132 comprises a belt that has been threaded around rollers 136, at least one of which is driven by a motor. The rollers 136 are mounted adjacent a periphery of the table such that each conveyor strip 132 acts as an endless conveyor that traverses longitudinally over the tire-facing surface 126 of the table 124. Four belts are shown, each having a width of about 1-inch. One or more motors used to operate the conveyor strips 132 are configured to move the strips in the same direction and speed during operation. In one embodiment, the motor(s) can be stepper motors that are mounted within the enclosure 112 below the table 124 and are connected to and controlled by a controller 138. The motor(s) can include a drive pulley that engages and pulls the belts around the rollers 136 to operate the conveyors. The controller 138 can be adapted to provide to the motors command signals indicative of the speed, direction and belt travel of the conveyor strips 132.

As shown in FIGS. 1 and 3, the machine 100 includes an incoming conveyor 202 and an outgoing conveyor 204 disposed at opposing longitudinal ends of the enclosure 112. The incoming and outgoing conveyors 202 and 204, along with the conveyor strips 132, are together configured to act as a conveying system 206 for loading a tire into a test area of the machine 100, passing the tire through the test area, and unloading the tire relative to the machine 100. More specifically, the incoming conveyor 202, which is shown in FIG. 1 with a conveyor belt removed, is arranged to stage tires for loading onto the table 124, and to move those tires close to the table and onto at least a lead portion of the conveyor strips 132 until the tire can be engaged by the strips 132 and carried fully onto the table 124. The conveyor strips 132 can convey the tire out of the testing area onto the outgoing conveyor 204 after the machine 100 has inspected the tire.

To help substantially center tires on the table 124 for testing, the incoming conveyor 202 can include a centering device 207, which is shown in the top view of FIG. 3. The centering device 207 is configured to align tires of various diameters in a transverse direction, Y (FIG. 3), relative to a transverse machine inspection centerline as the tires travel along the incoming conveyor 202 en route to the enclosure 112.

In one embodiment, the centering device 207 includes two alignment arms 210 and two linkages 212 pivotally connected at their ends to one another to form an M-shape. The base of the M-shape at the ends of the two arms 210 is pivotally connected to a frame 215 of the incoming conveyor 202. The two linkages 212 are connected at the other ends of the arms 210 and to one another to form the M-shape. A spring 216 or another resilient element can connect the pivot connecting the two linkages 212 to one another with the frame 214 such that, as a tire passes between the two arms 210 along the longitudinal direction X, the arms 210 cooperatively act upon the tire to adjust its position along the transverse direction Y to help align the center of the tire with the transverse machine inspection centerline. The two linkages 212 can be placed above, below or otherwise out of the path of the passing tire. The symmetrical transfer of spring force upon the tires passing between the two arms 210 helps transversely displace the tires as needed to one side or the other before settling in a position of the conveyor 202, which is substantially aligned in the transverse direction Y with the transverse machine inspection centerline (e.g., a central region of the table 124 in the enclosure 112).

Tires that are handed off to the conveyor strips 132 from the incoming conveyor 202 are carried onto the table 124. While carrying the tires onto the table 124, a sensor 214 (FIG. 2) monitors the longitudinal position of the tire relative to the table 124 and provides a signal indicative of that position to the controller 138. The controller 138, based on that signal, commands the conveyor strips 132 to continue advancing until the sensor 214 senses that the tire is disposed substantially centrally above the shearographic assembly 118. In one embodiment, the sensor 214 is a visual sensor such as a camera that acquires successive pictures of the tire and compares them to a position template for determining when a feature of the tire, for example, the central bead, is substantially concentric with an element of the template. In the illustrated embodiment, the sensor 214 is an infrared sensor that emits multiple beams that are received by corresponding receivers (not shown) disposed below the table 124. The passing tire interrupts these beams, which is sensed by the sensor and translated into the signal provided to the controller. When the beam interruption becomes symmetrical based on the placement of the receivers, the signal provided to the controller 138 is understood to indicate that the tire is centrally disposed and the conveyor strips 132 are stopped. In other embodiments, the controller 138 can use the signal from the sensor 214 to determine the overall dimension of the tire and, along with a determination of the speed of the conveyor strips 132, calculate the total conveyance time that is required to align the center of the tire with the shearographic assembly 118 within the enclosure 112.

After the tire has been centrally placed in the enclosure 112 relative to the shearographic assembly 118, one or more additional tires may be staged for loading into the machine on the incoming conveyor 202. These may all be the same or similar types of tires, or may alternatively mixed tire types and sizes. The upper shell 106 may be closed while testing a tire loaded onto the table 124. When testing is complete, the enclosure 112 may open and the conveyor strips 132 may be activated to carry the inspected tire onto the outgoing conveyor 204. At the same time, a tire to be inspected next may be loaded onto the incoming side of the conveyor strips 132. The tire passing off the conveyor strips 132 and onto the outgoing conveyor 204 may be carried off the enclosure 112 sufficiently to close the upper shell 106 over the next tire in position to be tested. In one embodiment, the outgoing conveyor 204 may act as a staging area and be sufficiently long to store thereon a number of inspected tires for unloading.

Figure 4:
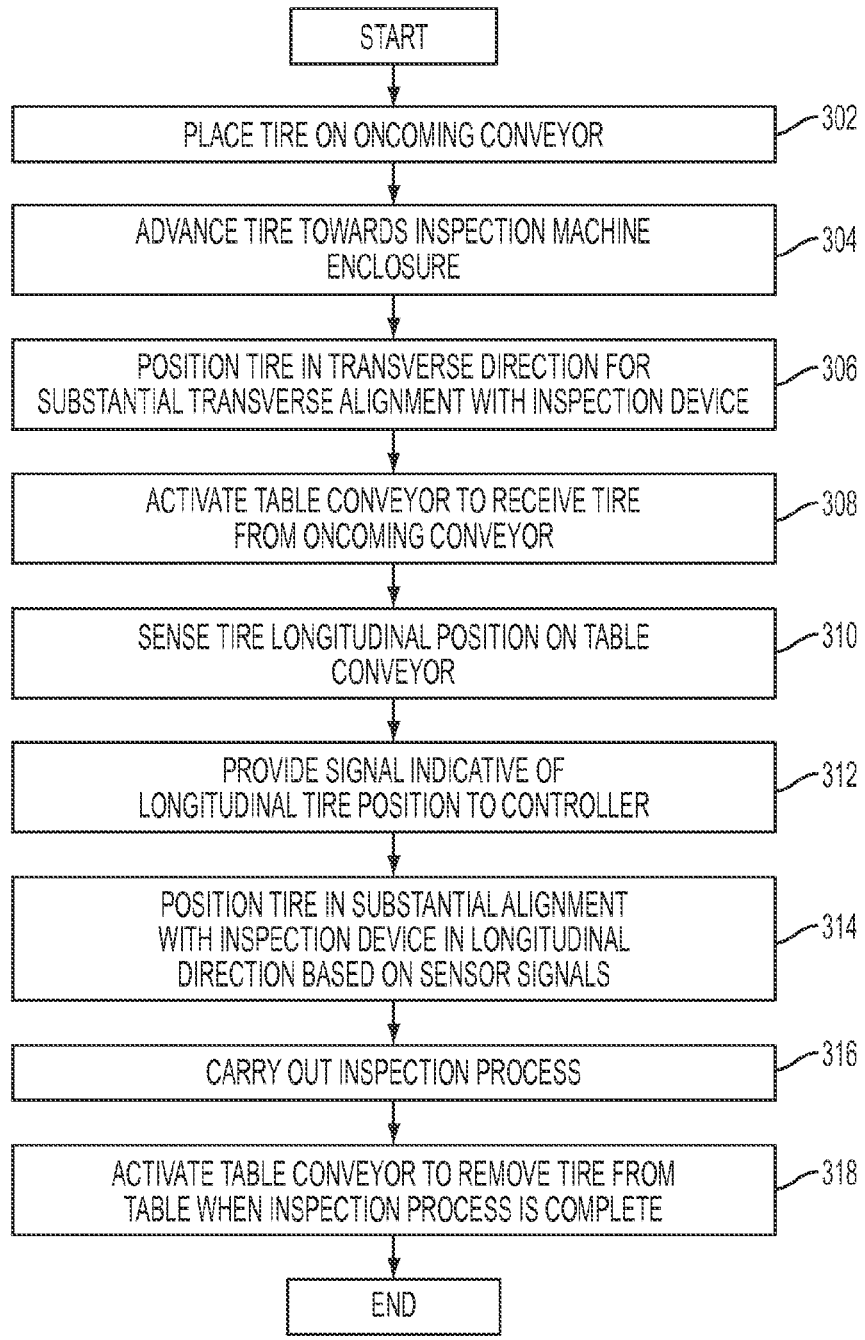
FIG. 4 is a flowchart of steps of an embodiment of a method of operating a shearographic tire imaging machine in accordance with principles of the disclosure.

A flowchart of illustrative steps of an embodiment of a method of operating a shearographic tire imaging machine is shown in FIG. 4. In embodiments, the machine may be the machine 100 as shown in FIGS. 1-3, which includes incoming and outgoing conveyors disposed around an inspection area that includes an additional positioning system for moving and properly positioning articles therein for inspection. A tire can be placed on an incoming conveyor at process step 302. The tire placed on the incoming conveyor may be a single tire for loading into an inspection enclosure of the machine or can be one of a plurality of tires that are staged for inspection and sequentially provided to the machine for inspection.

The machine may include an inspection device disposed at a particular location within the testing enclosure, and the tire to be inspected can be aligned in the longitudinal and the transverse directions X and Y with the inspection device. The incoming conveyor may advance the tire towards the enclosure of the inspection machine at process step 304, while simultaneously displacing the tire in the transverse direction for a desired alignment with the inspection device at 306. The alignment of the tire in the transverse direction may be accomplished by any appropriate fashion, for example, by electronically sensing a transverse position of the tire with sensors and using actuators to displace the tire until a desired transverse position is attained. In embodiments, transverse tire positioning can be accomplished by a spring-loaded guide that engages the tire periphery including an outer diameter of the tire, and applies force on either side of the tire such that the tire may assume a centrally located transverse position relative to the inspection device of the machine as the tire travels along the incoming conveyor towards the inspection machine enclosure.

A conveyor associated with a table disposed within the inspection enclosure of the machine is activated at process step 308 to receive the tire from the incoming conveyor. The table may have a central opening that is substantially aligned with the inspection device, and the conveyor may be partitioned in portions such as strips or belts that are disposed on both sides of the opening in the transverse direction such that the tire may be carried over the opening and aligned with the inspection device. In embodiments, the size and shape of the table opening, as well as the size, configuration and positioning of the table conveyor system can be arranged to provide a substantially unobstructed view of both sidewall portions of the tire by the shearographic assembly.

In one embodiment, a position of the tire is sensed using appropriate sensors at process step 310. The sensors may provide signals indicative of the longitudinal tire position to a controller at process step 312. The controller, which controls the conveyor to selectively adjust the direction, position and speed of conveyance of the tire, may position the tire in substantial alignment with the inspection device based on a position feedback of the tire position provided by the sensors at process step 314 by stopping, slowing down and/or reversing the motion of the conveyor, as appropriate, to place the tire above the inspection device.

When the tire is positioned for inspection, an inspection process can be carried out at process step 316. The inspection process may include various operations depending on the type and configuration of the inspection machine. In one embodiment, the inspection machine can be a shearographic inspection machine that includes shearographic emitter and receiver devices that can scan portions of the tire in various ambient conditions such as at atmospheric pressure and at positive or negative gage pressures. In embodiments, the shearographic assembly can be configured to scan both sidewall portions of the tire while the tire is disposed on the conveyor.

When the inspection process has been completed, the table conveyor may be activated at process step 318 to remove the tire from the table and convey it to an outgoing conveyor disposed downstream of the table in the longitudinal direction. The activation of the table conveyor at process step 318 may fulfill a double function of loading a subsequent tire into the machine while also off loading an inspected tire onto the outgoing conveyor.

In other embodiments, the outgoing conveyor may be one and the same as the incoming conveyor that operates in reverse. In still other embodiments, the table may be rotatable along its centerline to steer the tire onto more than one outgoing conveyor, for example, depending on the results of the inspection process. In this way, tires that are approved for further processing may be provided to one conveyor while tires having rejectable defects may be provided to a different conveyor. Even further, the various outgoing conveyors may be configured to receive tires of different sizes. In this way, as part of the tire sensing procedures, the controller may make a determination of the particular tire type such that various types of inspected tires can be sorted according to their type in the same machine by being provide a respective conveyor dedicated for a particular tire type.

What is claimed is:

1. A tire or casing inspection machine, comprising:
   a sealable enclosure formed within a housing, the sealable enclosure adapted to be selectively subjected to positive gage pressure and/or vacuum when testing a tire or casing disposed within the sealable enclosure;
   a table disposed within the sealable enclosure and connected to a portion of the housing, the table having an opening that is adapted to be aligned with a bead hole of the tire or casing disposed on the table;
   a shearographic assembly connected to the housing and disposed within the sealable enclosure in alignment with the opening of the table, the shearographic assembly being selectively moveable to protrude through the opening relative to the table and rotatable about an opening centerline such that it can scan multiple portions of the tire or casing disposed on the table from various perspectives;

at least two conveyor strips extending parallel to one another and associated with the table, the at least two conveyor strips being sized and positioned on the table such that they do not interfere with visibility of top and bottom sidewall portions of the tire or casing disposed on the table relative to the shearographic assembly, the at least two conveyor strips adapted to carry and selectively move the tire or casing relative to the machine.

2. The tire or casing inspection machine of claim 1, wherein the housing includes an upper shell having a rim, and a lower shell having a rim, wherein the upper shell is hingeably connected to the lower shell such that, when the upper and lower shells are in a closed position the sealable enclosure is defined therewithin when the respective rims are sealably engaged.

3. The tire or casing inspection machine of claim 1, further comprising:
 a controller associated with the shearographic assembly and the at least two conveyor strips;
 a sensor disposed to sense a position of the tire or casing relative to the table and provide a signal indicative of the position to the controller;
 wherein the controller operates to position the tire or casing such that the bead hole is substantially aligned with the opening in the table by activating the at least two conveyor strips to carry the tire or casing, and to activate the shearographic assembly to protrude from the table and be disposed within the bead hole for scanning the tire or casing.

4. The tire or casing inspection machine of claim 1, further comprising an incoming conveyor disposed adjacent the housing and adapted to stage and deliver the tire or casing to the at least two conveyor strips.

5. The tire or casing inspection machine of claim 4, further comprising a centering device disposed along the incoming conveyor, the centering device configured to align tires or casings of various diameters in a transverse direction that is perpendicular to a longitudinal direction of travel defined by the at least two strip conveyors.

6. The tire or casing inspection machine of claim 5, wherein the centering device comprises:
 two alignment arms, and
 two linkages pivotally connected at their ends to one another and a respective one of the two alignment arms to, together, form an M-shape, wherein a base of the M-shape at the ends of the two arms alignment arms is pivotally connected to a frame of the incoming conveyor; and
 a resilient element connected between the two linkages and the frame such that, when a tire or casing passes between the two alignment arms along a longitudinal direction, the two alignment arms cooperatively act upon the tire or casing to adjust a position thereof along a transverse direction to align a center of the tire or casing with a longitudinally extending machine centerline that coincides with a center of the opening in the table.

7. The tire or casing inspection machine of claim 1, wherein the shearographic assembly is configured to operate at two different heights relative to the table such that both sidewall portions of the tire or casing disposed on the table can be scanned without moving or flipping the tire or casing within the machine.

8. The tire or casing inspection machine of claim 1, wherein the machine comprises four conveyor strips disposed parallel to one another along a longitudinal direction, each of the four conveyor strips comprising:
 a belt that is threaded around rollers two or more rollers, at least one of said two or more rollers being driven by a motor;
 wherein the table has a generally circular shape that defines a periphery;
 wherein said rollers are mounted adjacent the periphery of the table such that each conveyor strip acts as an endless conveyor that traverses longitudinally over a tire-facing surface of the table;
 wherein the four conveyor strips are configured to move in the same direction and speed during operation.

9. A method for inspecting tires or casings, comprising:
 staging a tire adjacent an inspection machine, the inspection machine having a sealable enclosure;
 automatically advancing the tire towards the inspection machine when an inspection cycle is initiated;
 aligning the tire in a transverse direction relative to the inspection machine while the tire is advanced towards the inspection machine;
 opening the sealable enclosure to admit the tire onto an inspection table having a table opening;
 admitting the tire onto the inspection table in a transversely aligned condition relative to the table opening, and closing the sealable enclosure;
 conveying the tire on the table in a longitudinal direction;
 sensing a longitudinal position of the tire relative to the table opening, and conveying the tire sufficiently to longitudinally align the tire with the table opening;
 activating an inspection device to inspect the tire while the tire is longitudinally and transversely aligned with the table opening.

10. The method of claim 9, wherein sensing the longitudinal position of the tire is accomplished by a sensor that provides a position signal to a controller, and wherein conveying the tire on the table in the longitudinal direction is accomplished by operation of the controller such that longitudinal alignment of the tire with the table opening is carried out based on the position signal.

11. The method of claim 9, further comprising subjecting the sealable enclosure to positive gage pressure or vacuum during the inspection cycle.

12. The method of claim 9, wherein the inspection device is a shearographic inspection device, and wherein the method further comprises:
 raising the shearographic inspection device along an axis perpendicular to the table through the table opening when the tire is aligned therewith, and
 rotating the shearographic inspection device about the axis to entirely scan the tire.

13. The method of claim 9, wherein activating the inspection device is accomplished at a first height and at a second height relative to the table, the first height providing a line of sight to one of two sidewalls of the tire and the second height providing a line of sight to another of the two sidewalls of the tire relative to the inspection device, and wherein rotating the inspection device is repeated for each of the first and second heights to completely scan the tire without moving or flipping the tire during the inspection cycle.

14. The method of claim 9, wherein conveying the tire on the table includes operating at least two conveyor strips disposed parallel to one another along the longitudinal direction on the table, each of the at least two conveyor strips comprising:

a belt that is threaded around rollers two or more rollers, at least one of said two or more rollers being driven by a motor;

wherein the table has a generally circular shape that defines a periphery;

wherein said rollers are mounted adjacent the periphery of the table such that each conveyor strip acts as an endless conveyor that traverses longitudinally over a tire-facing surface of the table; and wherein the at least two conveyor strips are configured to move in the same direction and speed during operation.

15. The method of claim 9, wherein the sealable enclosure is defined within a housing, the housing including an upper shell having a rim, and a lower shell having a rim, wherein the upper shell is hingeably connected to the lower shell such that, when the upper and lower shells are in a closed position the sealable enclosure is defined therewithin when the respective rims are sealably engaged.

16. The method of claim 9, wherein aligning the tire in the transverse direction is accomplished by using a centering device disposed along an incoming conveyor associated with the machine, the centering device configured to align tires or casings of various diameters in the transverse direction that is perpendicular to the longitudinal direction.

17. The method of claim 16, wherein the centering device comprises:

two alignment arms, and two linkages pivotally connected at their ends to one another and to a respective one of the two alignment arms to, together, form an M-shape, wherein a base of the M-shape at the ends of the two arms alignment arms is pivotally connected to a frame of the incoming conveyor; and a resilient element connected between the two linkages and the frame such that, when a tire or casing passes between the two alignment arms along the longitudinal direction, the two alignment arms cooperatively act upon the tire or casing to adjust a position thereof along a transverse direction to align a center of the tire or casing with a longitudinally extending machine centerline that coincides with a center of the opening in the table.

18. A shearographic inspection machine, comprising:

an enclosure formed within a housing, the enclosure adapted to be selectively subjected to pressure or vacuum when testing a tire or casing disposed within the enclosure, the enclosure having a domed top portion and a generally cylindrical bottom portion, the top and bottom portions being sealably engageable along respective rims;

a generally circular table disposed within the enclosure, the table having a central opening that is adapted to be aligned with a bead hole of the tire or casing disposed on the table, the table being coplanar with the rim of the generally cylindrical bottom portion of the enclosure;

a shearographic assembly connected to the housing and disposed within the enclosure, the shearographic assembly being aligned with a centerline of the central opening, moveable to protrude through the central opening relative to the table, and rotatable about the centerline such that it can scan multiple portions of the tire or casing disposed on the table from various perspectives;

four conveyor strips extending parallel to one another and associated with the table, the four conveyor strips being sized and positioned on the table such that they do not interfere with visibility of top and bottom sidewall portions of the tire or casing disposed on the table relative to the shearographic assembly, the four conveyor strips being adapted to carry and selectively move the tire or casing relative to the machine;

an incoming conveyor disposed adjacent the housing and adapted to stage and deliver the tire or casing to the four conveyor strips;

a centering device disposed along the incoming conveyor, the centering device configured to align the tire or casing in a transverse direction that is perpendicular to a longitudinal direction of travel defined by the four conveyor strips;

a controller associated with the shearographic assembly and the four conveyor strips;

a sensor disposed to sense a position of the tire or casing relative to the table and provide a signal indicative of the position to the controller;

wherein the controller is disposed to position the tire or casing such that the bead hole is substantially aligned with the central opening in the table by activating the four conveyor strips to carry the tire or casing, and to activate the shearographic assembly to protrude from the table and be disposed within the bead hole for scanning the tire or casing.

19. The shearographic inspection machine of claim 18, wherein the centering device comprises:

two alignment arms, and two linkages pivotally connected at their ends to one another and to a respective one of the two alignment arms to, together, form an M-shape, wherein a base of the M-shape at the ends of the two arms alignment arms is pivotally connected to a frame of the incoming conveyor; and a resilient element connected between the two linkages and the frame such that, when a tire or casing passes between the two alignment arms along a longitudinal direction, the two alignment arms cooperatively act upon the tire or casing to adjust a position thereof along the transverse direction to align a center of the tire or casing with a longitudinally extending machine centerline that intersects the centerline of the central opening in the table.

20. The shearographic inspection machine of claim 18, wherein the shearographic assembly is configured to operate at two different heights relative to the table such that both sidewall portions of the tire or casing disposed on the table can be scanned without moving or flipping the tire or casing within the machine.

* * * * *